United States Patent
Kjaer et al.

(10) Patent No.: US 9,884,131 B2
(45) Date of Patent: Feb. 6, 2018

(54) POSITRON EMITTING RADIONUCLIDE LABELED PEPTIDES FOR HUMAN UPAR PET IMAGING

(71) Applicant: Curasight ApS, Copenhagen N (DK)

(72) Inventors: Andreas Kjaer, Frederiksberg (DK); Morten Persson, Copenhagen (DK); Jacob Madsen, Copenhagen (DK)

(73) Assignee: CURASIGHT APS, Copenhagen N (DK)

( * ) Notice: Subject to any disclaimer, the term of this patent is extended or adjusted under 35 U.S.C. 154(b) by 114 days.

(21) Appl. No.: 14/649,113

(22) PCT Filed: Nov. 29, 2013

(86) PCT No.: PCT/DK2013/050402
§ 371 (c)(1),
(2) Date: Jun. 2, 2015

(87) PCT Pub. No.: WO2014/086364
PCT Pub. Date: Jun. 12, 2014

(65) Prior Publication Data
US 2016/0263260 A1 Sep. 15, 2016

Related U.S. Application Data

(60) Provisional application No. 61/732,443, filed on Dec. 3, 2012.

(30) Foreign Application Priority Data

Dec. 3, 2012 (DK) ................. 2012 70751

(51) Int. Cl.
*A61K 51/00* (2006.01)
*A61M 36/14* (2006.01)
*A61K 51/08* (2006.01)
*A61K 38/08* (2006.01)

(52) U.S. Cl.
CPC ............ *A61K 51/088* (2013.01); *A61K 38/08* (2013.01); *A61K 51/08* (2013.01); *A61K 51/083* (2013.01)

(58) Field of Classification Search
CPC ....... A61K 51/00; A61K 51/08; A61K 51/088; A61K 51/083; A61K 38/00; A61K 38/08; A61K 2121/00; A61K 2123/00
USPC .......... 424/1.11, 1.65, 1.69, 1.81, 1.85, 1.89, 424/9.1, 9.2, 9.3, 9.4, 9.5, 9.6; 514/1, 514/1.1, 19, 2, 19.3, 19.4, 19.5, 19.6, 514/20.9, 21.1, 21.2, 21.3, 21.4, 21.5, 514/21.6, 21.7; 534/7, 10–16; 530/300, 530/317, 324, 325, 326, 327, 328
See application file for complete search history.

(56) References Cited

U.S. PATENT DOCUMENTS

| | | | |
|---|---|---|---|
| 6,227,818 B1 | 8/2001 | Mazar et al. | |
| 6,277,818 B1* | 8/2001 | Mazar ................ | A61K 49/0002 424/1.69 |
| 6,514,710 B1 | 2/2003 | Jones et al. | |
| 6,896,870 B1* | 5/2005 | Mazar .............. | A61K 47/48246 424/1.11 |
| 7,026,282 B1 | 4/2006 | Ploug et al. | |
| 8,568,689 B1* | 10/2013 | Cuthbertson ........ | A61K 51/088 424/1.11 |
| 2010/0233082 A1* | 9/2010 | Langstrom ........... | A61K 51/088 424/1.69 |

FOREIGN PATENT DOCUMENTS

| | | |
|---|---|---|
| CN | 102600489 A | 7/2012 |
| WO | WO 01/25410 A2 | 4/2001 |
| WO | WO 2006/036071 A2 | 4/2006 |

OTHER PUBLICATIONS

Persson et al, Nuclear Medicine and Biology, 2012, vol. 39, pp. 560-569.*
International Search Report dated Mar. 7, 2014 for International Patent Application No. PCT/DK2013/050402, filed Nov. 29, 2013.
Denholt, C.L. et al.: "Evaluation of 4-[18F]fluorobenzoyl-FALGEA-NH2 as a positron emission tomography tracer for epidermal growth factor receptor mutation variant III imaging in cancer", Nuclear Medicine and Biology, 2011, vol. 38, No. 4, pp. 509-515.
Dijkgraaf et al. "PET of tumors expressing gastrinreleasing peptide receptor with an 18F-labeled bombesin analog", J Nuc/ Med. Jun. 2012; 53(6):947-952.
D'Souza CA et al.: "Highyielding aqueous 18F-labeling of peptides via Al18F chelation", Bioconjug Chem. Sep. 21, 2011 ;22(9):1793-1803.
Erik S Mittra et al: "Pilot Pharmacokinetic and Dosimetric Studies of 18 F-FPPRGD2: A PET Radiopharmaceutical Agent for Imaging a v b 3 Integrin Levels 1", Radiology, Jul. 1, 2011 (Jul. 1, 2011), pp. 182-191, XP055288163, DOI: 10.1148/radiol.11101139/-/DC1 Retrieved from the Internet: URL:http://pubs.rsna.org/doi/pdf/10.1148/radiol.11101139 [retrieved on Jul. 13, 2016].
European Search Report and Written Opinion for corresponding European Patent Application No. 13 860 317.0, dated Jul. 13, 2016.
Fournier, P. et al.: "Comparative study of 64Cu/NOTA-[D-Tyr6,βAla11,Thi13,Nle14]BBN(6-14) monomer and dimers for prostate cancer PET imaging", EJNMMI research, 2012, vol. 2, p. 8.
Gao H. et al. "PET imaging of angiogenesis after myocardial infarction/reperfusion using a one-step labeled integrin-targeted tracer 18F-AIF-NOTAPRGD2", EurJ Nuc/ Med Mo/ Imaging, Apr. 2012; 39(4):683-692.
Gupta A. et al.: Predictive value of the differential expression of the urokinase plasminogen activation axis in radical prostatectomy patients. Eur Urol. May 2009; 55(5):1124-1133.

(Continued)

*Primary Examiner* — D L Jones
(74) *Attorney, Agent, or Firm* — Merchant & Gould P.C.

(57) ABSTRACT

There is provided a positron-emitting radionuclide labelled peptide for non-invasive PET imaging of the Urokinase-type Plasminogen Activator Receptor (uPAR) in humans. More specifically the invention relates to human uPAR PET imaging of any solid cancer disease for diagnosis, staging, treatment monitoring and especially as an imaging biomarker for predicting prognosis, progression and recurrence.

6 Claims, 8 Drawing Sheets

(56) References Cited

OTHER PUBLICATIONS

Heribert Hanscheid et al: "PET SUV correlates with radionuclide uptake in peptide receptor therapy in meningioma", European Journal of Nuclear Medicine Andmolecular Imaging, Springer, Berlin, DE, vol. 39, No. 8, Apr. 20, 2012 (Apr. 20, 2012), pp. 1284-1288, XP035079901, ISSN: 1619-7089, DOI: 10.1007/500259-012-2124-X.

Heskamp S. et al.: "Imaging of human epidermal growth factor receptor type 2 expression with 18F-labeled affibody molecule ZHER2:2395 in a mouse model for ovarian cancer". J Nucl Med. Jan. 2012; 53(1):146-153.

Hoigebazar L. et al.: "Syntheses of 2-nitroimidazole derivatives conjugated with 1,4, 7-triazacyclononane-N, N'-diacetic acid labeled with F-18 using an aluminum complex method for hypoxia imaging". J Med Chem. Apr. 12, 2012; 55(7):3155-3162.

Kjellman A. et al.: "Soluble urokinase plasminogen activator receptor as a prognostic marker in men participating in prostate cancer screening", J Intern Med. Mar. 2011; 269(3):299-305.

Kriegbaum MC et al.: "Rational targeting of the urokinase receptor (uPAR): development of antagonists and non-invasive imaging probes", Curr Drug Targets. Nov. 2011; 12(12): 1711-1728.

Kurdziel KA et al. "The Kinetics and Reproducibility of 18FSodium Fluoride for Oncology Using Current PET Camera Technology". J Nucl Med. Aug. 2012; 53(8): 1175-1184.

Laverman P. et al. "A novel facile method of labeling octreotide with (18)F-fluorine", J Nucl Med. Mar. 2010; 51 (3):454-461.

Laverman P. et al.: "Optimized labeling of NOTA-conjugated octreotide with F-18". Tumour Biol. Apr. 2012; 33(2):427-434.

Liu S. et al.: "One-step radiosynthesis of (1)(8)F-AlF-NOTA-RGD(2) for tumor angiogenesis PET imaging", Eur J Nucl Med Mo/Imaging. Sep. 2011; 38(9):1732-1741.

Liu, Z. et al.: "18F, 64Cu, and 68Ga Labeled RGD-Bombesin Heterodimeric Peptides for PET Imaging of breast Cancer", Bioconjugate Chemistry, 2009, vol. 20, No. 5, pp. 1016-1025.

Liu, Z. et al.: "Small-Animal PET of Tumors with 64Cu-Labeled RGD-Bombesin Heterodimer", Journal of Nuclear Medicine, 2009, vol. 50, No. 7, pp. 1168-1177.

Margheri F. et al.: "Effects of blocking urokinase receptor signaling by antisense oligonucleotides in a mouse model of experimental prostate cancer bone metastases", Gene Ther. Apr. 2005; 12(8):702-714.

McBride WJ et al.: "A novel method of 18F radiolabeling for PET". J Nucl Med. Jun. 2009; 50(6):991-998.

McBride WJ et al.: "Improved 18F labeling of peptides with a fluoride-aluminum-chelate complex", Bioconjug Chem. Jul. 21, 2010; 21(7):1331-1340.

McBride WJ et al.: "The radiolabeling of proteins by the [18F]AlF method", Appl Radiat Isot. Jan. 2012; 70(1):200-204.

Miyake H. et al.: "Elevation of serum levels of urokinase-type plasminogen activator and its receptor is associated with disease progression and prognosis in patients with prostate cancer", Prostate. May 1999; 39(2): 123-129.

Miyake H. et al.: "Elevation of urokinasetype plasminogen activator and its receptor densities as new predictors of disease progression and prognosis in men with prostate cancer", Int J Oncol. Mar. 1999; 14(3):535-541.

Nogueira L. et al.: "Other biomarkers for detecting prostate cancer", BJU Int, Jan. 2010; 105(2):166-169.

Persson M. et al.: "New peptide receptor radionuclide therapy of invasive cancer cells: in vivo studies using (177)Lu-DOTA-AE105 targeting uPAR in human colorectal cancer xenografts", Nuc/ Med Biol. Jun. 25, 2012.

Persson, M. et al.: "68Ga-labeling and in vivo evaluation of a uPAR binding DOTA- and NODAGA-conjugated peptide for PET imaging of invasive cancers", Nuclear Medicine and Biology, vol. 39, May 2012 (May 2012), pp. 560-569, XP002750159.

Persson, M. et al.: "Quantitative PET of Human Urokinase Type Plasminogen Activator Receptor with 64Cu-DOTA-AE105: Implications for Visualizing Cancer Invasion", The Journal of Nuclear Medicine, vol. 53, No. 1, Jan. 2012 (Jan. 2012 ), pp. 138-145, XP055228626.

Piironen T. et al.: "Enhanced discrimination of benign from malignant prostatic disease by selective measurements of cleaved forms of urokinase receptor in serum", Clin Chem. May 2006; 52(5):838-844.

Ploug M et al.: "Peptide-derived antagonists of the urokinase receptor. Affinity maturation by combinatorial chemistry, identification of functional epitopes, and inhibitory effect on cancer cell intravasation". Biochemistry. Oct. 9, 2001; 40(40):12157-12168.

Ploug M. "Structure-function relationships in the interaction between the urokinase-type plasminogen activator and its receptor". Curr Pharm Des. 2003; 9(19): 1499-1528.

Pulukuri SM et al.: "RNA interference-directed knockdown of urokinase plasminogen activator and urokinase plasminogen activator receptor inhibits prostate cancer cell invasion, survival, and tumorigenicity in vivo", J Biol Chem. Oct. 28, 2005; 280(43):36529-36540.

Rabbani SA et al.: "An anti-urokinase plasminogen activator receptor antibody (ATN-658) blocks prostate cancer invasion, migration, growth, and experimental skeletal metastasis in vitro and in vivo", Neoplasia. Oct. 2010; 12(10):778-788.

Rasch M.G. et al.: "Intact and cleaved uPAR forms: diagnostic and prognostic value in cancer", Frontiers in Bioscience, May 1, 2008; vol. 13, pp. 6752-6762.

Shariat SF et al.: "Association of the circulating levels of the urokinase system of plasminogen activation with the presence of prostate cancer and invasion, progression, and metastasis", J Clin Oncol. Feb. 1, 2007; 25(4):349-355.

Shariat SF et al.: "Tumor markers in prostate cancer I: blood-based markers", Acta Oncol., Jun. 2011; 50 Suppl 1, pp. 61-75.

Steuber T. et al.: "Free PSA isoforms and intact and cleaved forms of urokinase plasminogen activator receptor in serum improve selection of patients for prostate cancer biopsy", Int J Cancer, Apr. 1, 2007; 120(7):1499-1504.

Traub-Weidinger T et al: "Preliminary experience with (68)Ga-DOTA-lanreotide positron emission tomography.", The Quarterly Journal of Nuclear Medicine and Molecular Imaging, vol. 54, No. 1, Feb. 2010 (Feb. 2010), pp. 52-60, ISSN: 1824-4785.

Z.-B. Li et al: "Imaging of Urokinase-Type Plasminogen Activator Receptor Expression Using a 64Cu-Labeled Linear Peptide Antagonist by microPET", Clinical Cancer Research, vol. 14, No. 15, Aug. 1, 2008 (Aug. 1, 2008), pp. 4758-4766, XP055288104.

Skovgaard et al., "Safety, Dosimetry, and Tumor Detection Ability of 68Ga-NOTA-AE105: First-in-Human Study of a Novel Radioligand for uPAR PET Imaging," The Journal of Nuclear Medicine, vol. 58, No. 3, (2017).

* cited by examiner

POSITRON EMITTING RADIONUCLIDE LABELED PEPTIDES FOR HUMAN UPAR PET IMAGING

This application is a National Stage Application of PCT/DK2013/050402, filed 29 Nov. 2013, which claims benefit of Serial No. 2012 70751, filed 3 Dec. 2012 in Denmark, and which claims benefit of Ser. No. 61/732,443, filed 3 Dec. 2012 in the United States, and which application(s) are incorporated herein by reference. To the extent appropriate, a claim of priority is made to each of the above disclosed applications.

FIELD OF THE INVENTION

The present invention relates to a positron-emitting radionuclide labelled peptide for noninvasive PET imaging of the Urokinase-type Plasminogen Activator Receptor (uPAR) in humans. More specifically the invention relates to human uPAR PET imaging of any solid cancer disease for diagnosis, staging, treatment monitoring and especially as an imaging biomarker for predicting prognosis, progression and recurrence.

BACKGROUND OF THE INVENTION

Urokinase-type plasminogen activator receptor (uPAR) is over-expressed in a variety of human cancers[1], including prostate cancer (PC), where uPAR expression in tumor biopsies and shed forms of uPAR in plasma have been found to be associated with advanced disease and poor prognosis[2-9]. Moreover, in patients with localized PC, high preoperative plasma uPAR levels have been shown to correlate with early progression[10]. Consistent with uPARs important role in cancer pathogenesis, through extracellular matrix degradation facilitating tumor invasion and metastasis, uPAR is considered an attractive target for both therapy[11-13] and imaging 14 and the ability to non-invasively quantify uPAR density in vivo is therefore crucial.

Radiolabeling and in vivo evaluation of a small peptide radiolabeled with Cu-64[15] and Ga-68[16] have been described for PET imaging of uPAR in various human xenograft cancer models. Such tracers could specifically differentiate between tumors with high and low uPAR expression and furthermore established a clear correlation between tumor uptake of the uPAR PET probe and the expression of uPAR[15]. However, $^{18}$F ($t_{1/2}$=109.7 min; β+, 99%) is considered the ideal short-lived PET isotope for labeling of small molecules and peptides due to the high positron abundance, optimal half-life and short positron range.

Recently, an elegant one step radiolabeling approach was developed for radiofluorination of both small peptides and proteins based on complex binding of $(Al^{18}F)^{2+}$ using 1,4,7-triazacyclononane (NOTA) chelator[17-20]. In this method, the traditional critical azeotropic drying step for 18F-fluoride is not necessary, and the labeling can be performed in water. A number of recently published studies have illustrated the potential of this new $^{18}$F-labeling method, where successful labeling of ligands for PET imaging of angiogenesis[21,22], Bombesin[23], EGFR[24] and hypoxia[25] have been demonstrated.

Various radio-labelled peptide compositions have been developed or are under development for site-specific targeting of various antigens, receptors and transporters for PET imaging. The general principle involves attaching a selected positron emitting radionuclide to a peptide and/or protein having a high specificity for a particular antigen for visualize and quantify the expressing and/or activity level using PET imaging. This field of research has shown particular applicability for tumor diagnosis, staging and treatment monitoring. A particularly desirable tumor antigen is uPAR in many different solid tumors including but not limited to non-small cell lung carcinomas, brain tumors, prostate tumors, breast tumors, colorectal tumors, pancreatic tumors and ovarian tumors.

DOTA (1,4,7,10-tetrakis(carboxymethyl)-1,4,7,10 tetraazacyclo dodecane) and its derivatives constitute an important class of chelators for biomedical applications as they accommodate very stably a variety of di- and trivalent metal ions. An emerging area is the use of chelator conjugated bioactive peptides for labelling with radiometals in different fields of diagnostic and therapeutic nuclear oncology. NOTA and its derivatives constitute another important class of chelators for biomedical applications.

uPAR PET imaging has been exploited in several human cancer xenograft models using a small linear DOTA-conjugated peptide, DOTA-AE105 radiolabeled with $^{64}$Cu (Li et al, 2008, Persson et al, 2011) and $^{68}$Ga (Persson et al, 2012) and using NODAGA (NODAGA-AE105) radiolabeled with $^{68}$Ga (Persson et al, 2012).

Malignant tumors are capable of degrading the surrounding extracellular matrix, resulting in local invasion or metastasis. Urokinase-type plasminogen activator (uPA) and its cell surface receptor (uPAR) are central molecules for cell surface-associated plasminogen activation both in vitro and in vivo. High expression of uPA and uPAR in many types of human cancers correlate with malignant tumor growth and associate with a poor prognosis, possibly indicating a causal role for the uPA/uPAR system in cancer progression and metastasis. Studies by immunohistochemistry and in situ hybridization indicate that expression levels of the components from the uPA system are generally very low in normal tissues and benign lesions. It has also been reported that the uPA/uPAR system is involved in regulating cell-extracellular matrix interactions by acting as an adhesion receptor for vitronectin and by modulating integrin function. Based on these properties, the uPA/uPAR system is consequently considered an attractive target for cancer therapy.

WO 01/25410 describes diagnostically or therapeutically labelled uPAR-targeting proteins and peptides. The peptide or protein comprises at least 38 amino acid residues, including residues 13-30 of the uPAR binding site of uPA.

U.S. Pat. No. 6,277,818 describes uPAR-targeting cyclic peptide compounds that may be conjugated with a diagnostic label. The peptides are based on the amino acid residues 20-30 of uPA.

U.S. Pat. No. 6,514,710 is also directed to cyclic peptides having affinity for uPAR. The peptides may carry a detectable label. The peptide comprises 11 amino acids joined by a linking unit.

Ploug et al. in Biochemistry 2001, 40, 12457-12168 describes uPAR targeting peptides but not in the context of imaging, including amino acid sequences as described in the present document. Similar disclosure is provided in U.S. Pat. No. 7,026,282.

The efficient targeting of uPAR demands a selective high-affinity vector that is chemically robust and stable.

SUMMARY OF THE INVENTION

The present inventors have surprisingly found that [$^{68}$Ga]-, [$^{64}$Cu]- and [Al$^{18}$F]-NOTA-AE105 have superior in vivo characteristics as a uPAR PET ligand, with high and specific tumor uptake, thus resulting in a high tumor-tobackground ratio and thereby superior contrast as a PET ligand for uPAR expression tumors. The inventors have found that both [$^{68}$Ga]- and [$^{64}$Cu]-NOTA-AE105 was able to specifically detect uPAR expressing human-derived brain tumor lesions in a orthotropic human cancer mouse model. Moreover, [Al 18F]-NOTA-AE105 was useful to detect uPAR positive human prostate cancer lesions after subcutaneously inoculation in mice. Overall, the radiolabeling of NOTA-AE105 with $^{18}$F, $^{68}$Ga and $^{64}$Cu, thus enable the visualization and quantification of uPAR using PET Imaging. This is a major improvement in PET Imaging.

The present invention thus provides a positron-emitting radionuclide labelled peptide conjugate for use in the prediction/diagnosis of aggressiveness, prognosis, progression or recurrence by PET imaging of uPAR expressing, and in particular uPAR overexpressed tumors, said conjugate comprising a uPAR binding peptide coupled via a chelating agent or covalently to a radionuclide selected from 18F, 64Cu, 68Ga, 66Ga, 60Cu, 61Cu, 62Cu, 89Zr, 124I, 76Br, 86Y, and 94mTc, wherein the conjugate is administered in a diagnostically effective amount, such as a dose of 100-500 MBq followed by PET scan ½-24 h after the conjugate has been administered, and quantification through SUVmax and/or SUVmean.

In a preferred embodiment the peptide is selected from the group consisting of:
(D-Asp)-([beta]-cyclohexyl-L-alanine)-(Phe)-(D-Ser)-(D-Arg)-(Tyr)-(Leu)-(Trp)-(Ser),
(Ser)-(Leu)-([beta]-cyclohexyl-L-alanine)-(Phe)-(D-Ser)-(Gln)-(Tyr)(Leu)-(Trp)-(Ser),
(D-Glu)-([beta]-cyclohexyl-L-alanine)-(Phe)-(D-Ser)-(D-Tyr)-(Tyr)-(Leu)-(Trp)-(Ser),
(Asp)-([beta]-cyclohexyl-L-alanine)-(Phe)-(D-Ser)-(D-Arg)-(Tyr)-(Leu)-(Trp)-(Ser),
(Asp)-([beta]-cyclohexyl-L-alanine)-(Phe)-(Ser)-(D-Arg)-(Tyr)-Leu)-(Trp)-(Ser),
(D-Asp)-([beta]-cyclohexyl-L-alanine)-(Phe)-(Ser)-(D-Arg)-(Tyr)-Leu)-(Trp)-(Ser),
(D-Thr)-([beta]-cyclohexyl-L-alanine)-(Phe)-(D-Ser)-(D-Arg)-(Tyr)-(Leu)-(Trp)-(Ser),
(D-Asp)-([beta]-cyclohexyl-L-alanine)-(Phe)-(D-Ser)-(D-Arg)-(Tyr)-(Leu)-([beta]-2-naphthyl-L-alanine)-(Ser),
(Asp)-([beta]-cyclohexyl-L-alanine)-(Phe)-(D-Ser)-(Arg)-(Tyr)-(Leu)-(Trp)-(Ser),
(Asp)-([beta]-cyclohexyl-L-alanine)-(Phe)-(D-Ser)-(D-Arg)-(Tyr)-(Leu)([beta]-1-naphthyl-L-alanine)-(Ser),
(D-Glu)-([beta]-cyclohexyl-L-alanine)-(Phe)-(D-Ser)-(Tyr)-(Tyr)-(Leu)-(Trp)-(Ser),
(Asp)-([beta]-cyclohexyl-L-alanine)-(Phe)-(D-Ser)-(D-Arg)-(Leu)-(Leu)-(Trp)-(D-H is),
(Asp)-([beta]-cyclohexyl-L-alanine)-(Phe)-(D-Ser)-(D-Arg)-([beta]-cyclohexyl-L-alanine)-(Leu)-(Trp)-(Ile),
(Asp)-([beta]-cyclohexyl-L-alanine)-(Phe)-(D-Ser)-(D-Arg)-(Tyr)-(Leu)([beta]-1-naphthylL-alanine)-(D-His),
(Asp)-([beta]-cyclohexyl-L-alanine)-(Phe)-(D-Ser)-(D-Arg)-(N-(2,3-dimethoxybenzyl)glycine)-(D-Phe)-(N-(3-indolylethyl)glycine)-(N-(2-methoxyethyl)glycine),
(Asp)-([beta]-cyclohexyl-L-alanine)-(Phe)-(D-Ser)-(D-Arg)-(N-(2,3-dimethoxybenzyl)glycine)-(D-Phe)-(N-benzylglycine)-(N-(2[beta]thoxyethyl)glycine),
(Asp)-([beta]-cyclohexyl-L-alanine)-(Phe)-(D-Ser)-(D-Arg)-(N-(2,3-dimethoxybenzyl)glycine)-(D-Phe)-(N-(methylnaphthalyl)glycine)-(N-(2-methoxyethyl)glycine), and
(Asp)-([beta]-cyclohexyl-L-alanine)-(Phe)-(D-Ser)-(D-Arg)-(N-(2,3-dimethoxybenzyl)glycine)-(D-Phe)-(N-(2,3-dimethoxybenzyl)glycine)-(Ile).

For all peptides mentioned, the C-terminal can be either with a carboxylic acid or an amide.

Preferably the chelating agent is DOTA, NOTA, CB-TE2A or NODAGA, and preferably the peptide is (D-Asp)-([beta]-cyclohexyl-L-alanine)-(Phe)-(D-Ser)-(D-Arg)-(Tyr)-(Leu)(Trp)-(Ser).

Particularly preferred are the conjugates having the formulas:

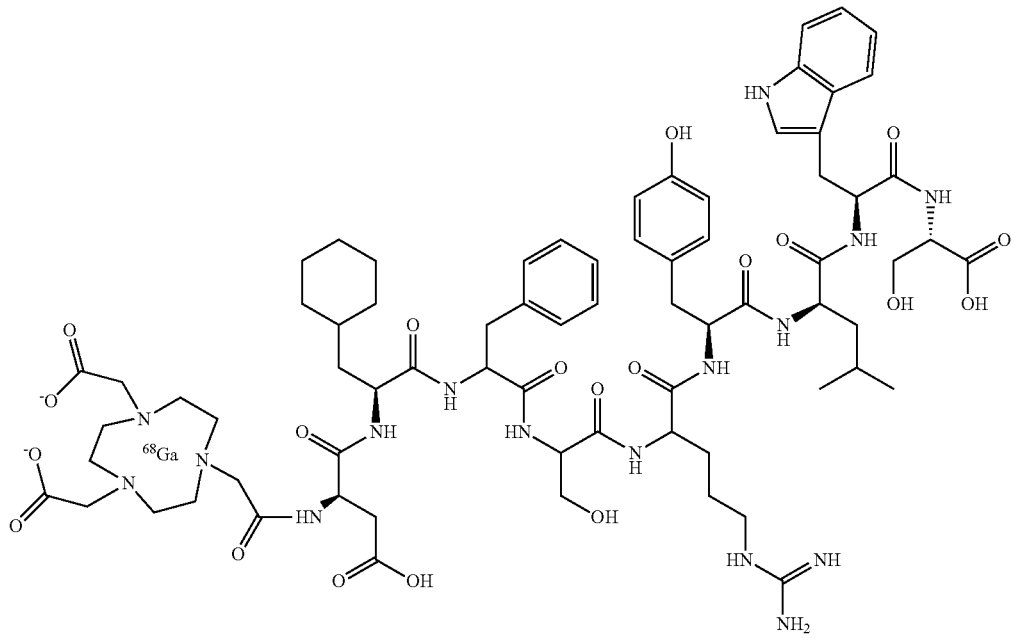

-continued
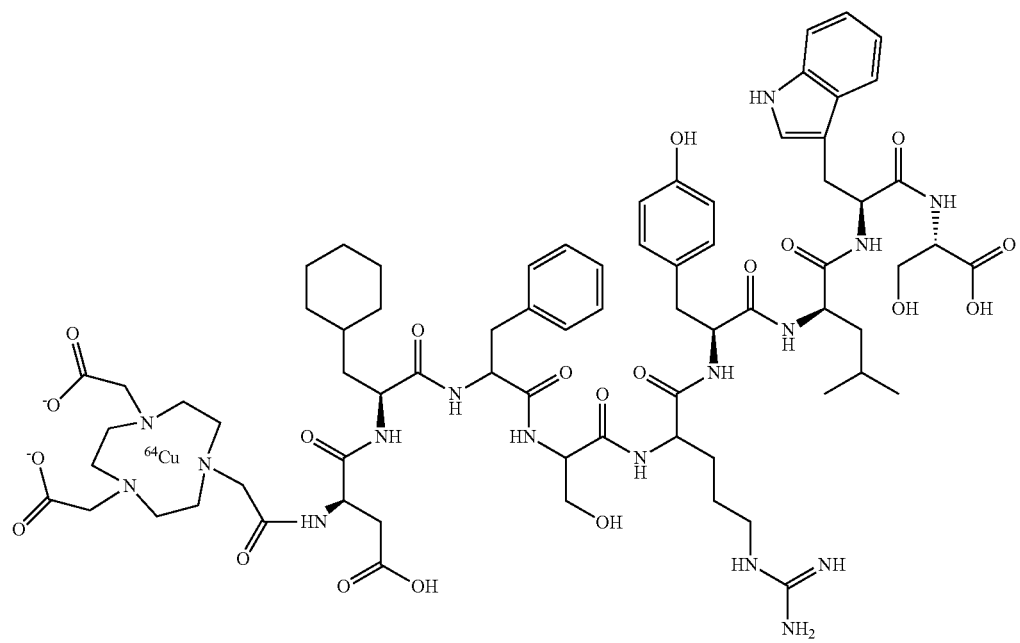
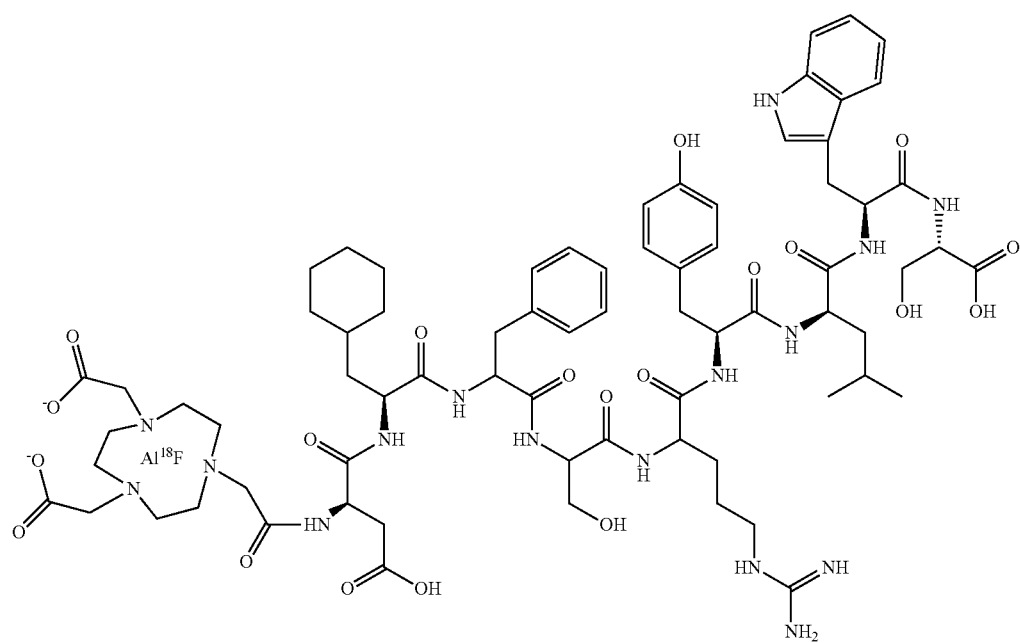

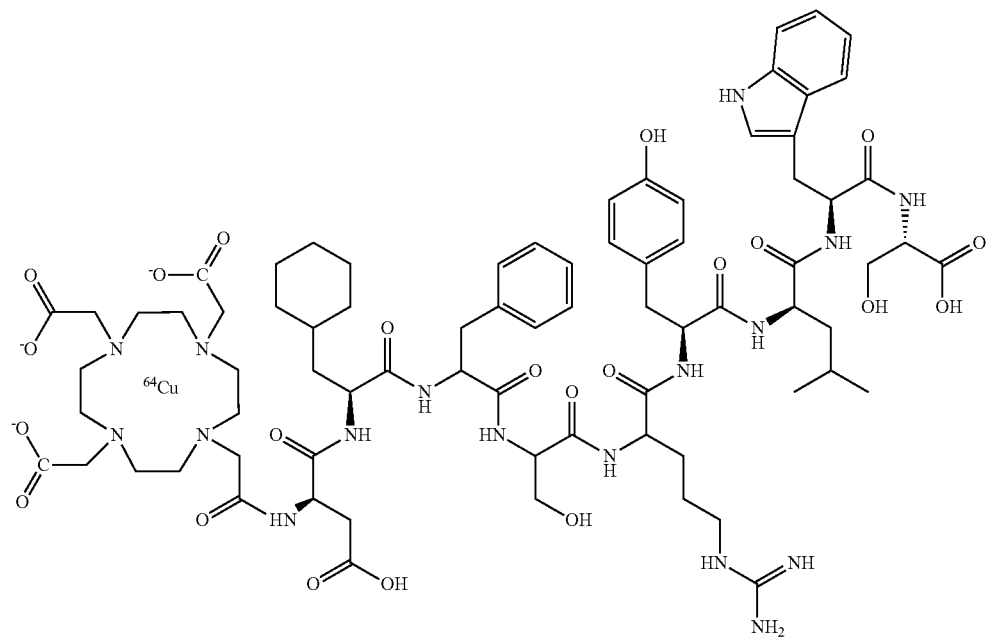
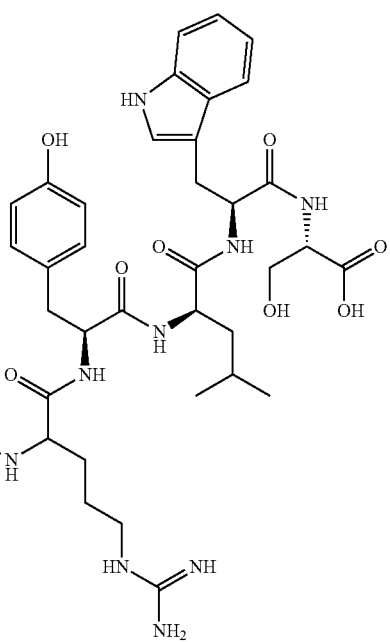

The present inventors have surprisingly found that the conjugates of the present invention are particularly useful in predicting aggressiveness, prognosis, progression or recurrence by PET imaging of uPAR expressing tumors, in particular prostate, breast, pancreatic, lung, brain and colorectal cancer.

The present invention also provides a method for predicting/diagnosing the aggressiveness, prognosis, progression or recurrence of uPAR overexpressed tumors, wherein the method comprises the steps of:

administrating a conjugate of the present invention in a diagnostically effective amount, such as a dose of 100-500 MBq;

PET scanning ½-24 h after the conjugate has been administered.

quantifying through SUVmax and/or SUVmean the absorption/binding of the conjugate in the tumor.

The steps carried out in accordance with the present invention can be summarized with the flow diagram shown in FIG. 8.

The present conjugates for use in accordance with the present invention can discriminate between uPAR expression levels in the primary tumor and metastases. Also, the use of quantification e.g. SUVmean and especially SUVmax can predict prognosis, progression and recurrence. The positron-emitting radionuclide labelled peptides of the present invention specifically target uPAR-positive cancer cells and/or uPAR positive stroma cells surrounding the cancer such as neutrophils and macrophages, and in particular the most aggressive (metastatic) cells. Moreover, the peptides of the present invention can be used for non-invasive detection and quantification of the expression level of uPAR using PET imaging. No current methods measuring uPAR is capable of this non-invasively in humans.

DETAILED DESCRIPTION OF THE INVENTION

Figure 1:
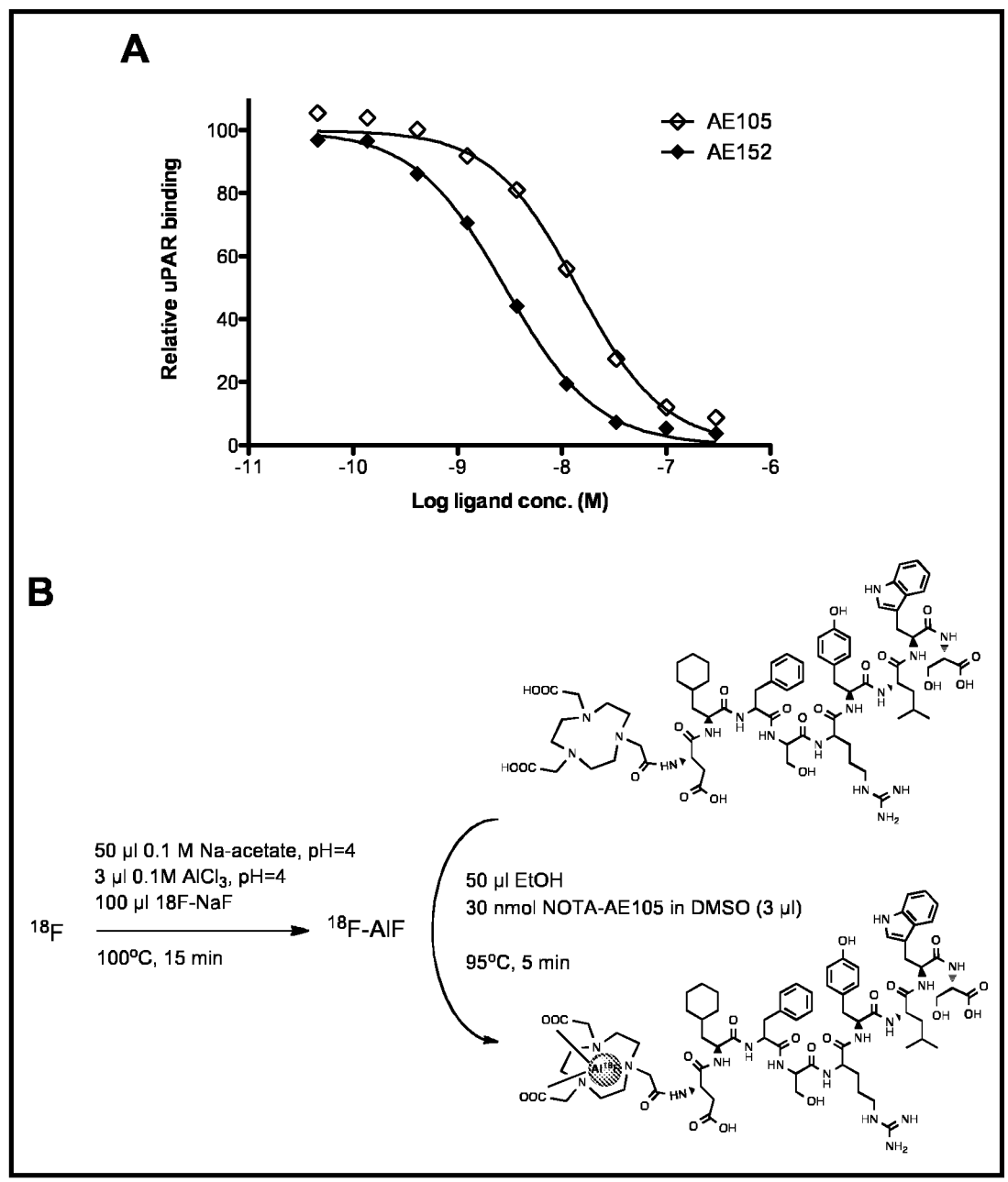
FIG. 1 shows: A. In vitro competitive inhibition of the uPA:uPAR binding for AE105 and AE152 using surface Plasmon resonance. B. Radiolabeling method for $^{18}$F—AlF-NOTAAE105.

Surprisingly, a radiolabeled peptide of the present invention is very useful in the prediction of cancer metastasis of uPAR expressing tumors.

The peptides selected for use in the conjugates of the present invention are typically radiolabeled by coupling a chelating agent to the peptide. The chelating agent is capable of binding a selected radionuclide thereto. The chelating agent and radionuclide is coupled to the peptide in a manner that does not interfere or adversely affect the binding properties or specificity of the peptide. The use of various chelating agents for radio labelling of peptides is well known in the art. The chelating agent is coupled to the peptide by standard methodology known in the field of the invention and may be added at any location on the peptide provided that the biological activity of the peptide is not adversely affected. Preferably, the chelating group is covalently coupled to the amino terminal amino acid of the peptide. The chelating group may advantageously be attached to the peptide during solid phase peptide synthesis or added by solution phase chemistry after the peptide has been obtained. Preferred chelating groups include DOTA, NOTA, NODAGA or CB-TE2A.

Concerning the synthesis of the peptides used in the present invention reference is made to U.S. Pat. No. 7,026,282.

The peptide/chelate conjugates of the invention are labeled by reacting the conjugate with radionuclide, e.g. as a metal salt, preferably water soluble. The reaction is carried out by known methods in the art.

The conjugates of the present invention are prepared to provide a radioactive dose of 35 between about 100-500 MBq (in humans), preferably about 200-400 MBq, to the individual. As used herein, "a diagnostically effective amount" means an amount of the conjugate sufficient to permit its detection by PET. The conjugates may be administered intravenously in any conventional medium for intravenous injection. Imaging of the biological site may be effected within about 30-60 minutes post-injection, but may also take place several hours post-injection. Any conventional method of imaging for diagnostic purposes may be utilized.

The following example focuses on the specific conjugate denoted $^{18}$F—AlF-NOTA-AE105. Other conjugates within the scope of the claims herein will be apparent to one skilled in the art from consideration of the specification or practice of the invention as disclosed herein.

The following chemistry applies to the Examples:

AE105 (Asp-Cha-Phe-Ser-Arg-Tyr-Leu-Trp-Ser-OH) (1)

The peptide according to the above mentioned sequence was synthesized by standard solid-phase peptide chemistry. NOTA-AE105 (NOTA-Asp-Cha-Phe-Ser-Arg-Tyr-Leu-Trp-Ser-OH)

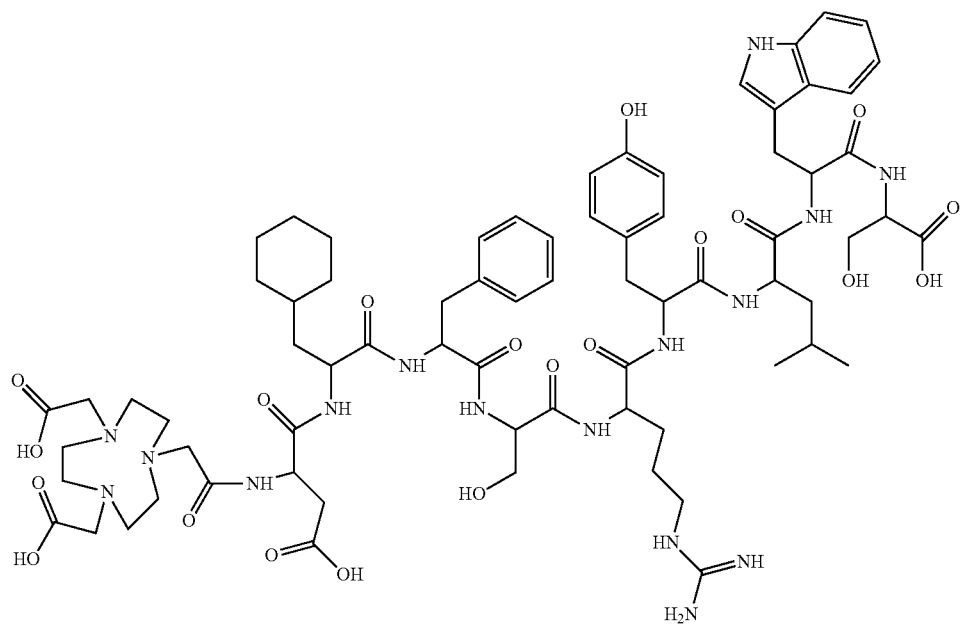 [SMILES: CC(C)CC(NC(=O)C(Cc1ccc(O)cc1)NC(=O)C(CCCNC(=N)N)NC(=O)C(CO)NC(=O)C(Cc1ccccc1)NC(=O)C(CC1CCCCC1)NC(=O)C(CC(=O)O)NC(=O)CN1CCN(CC(=O)O)CCN(CC(=O)O)CC1)C(=O)NC(Cc1c[nH]c2ccccc12)C(=O)NC(CO)C(=O)O]

The product is purified by RP-HPLC and analysed by RP-HPLC (retention time: 11.5 min, purity >98%) and electrospray-MS (1510.8 m.u.).

Example 1

The aim of the present study was to synthesize a NOTA-conjugated peptide and use the Al$^{18}$F method for development for the first $^{18}$F-labeled PET ligand for uPAR PET imaging and to perform a biological evaluation in human prostate cancer xenograft tumors. To achieve this, the present inventors synthesized high-affinity uPAR binding peptide denoted AE105 and conjugated NOTA in the N-terminal. $^{18}$F-labeling was done according to a recently optimized protocol[26]. The final product ($^{18}$F—AlF-NOTA-AE105) was finally evaluated in vivo using both microPET imaging in human prostate tumor bearing animals and after collection of organs for biodistribution study.

Chemical Reagents

All chemicals obtained commercially were of analytical grade and used without further purification. No-carrier-added $^{18}$F-fluoride was obtained from an in-house PETtrace cyclotron (GE Healthcare). Reverse-phase extraction C18 Sep-Pak cartridges were obtained from Waters (Milford, Mass., USA) and were pretreated with ethanol and water before use. The syringe filter and polyethersulfone membranes (pore size 0.22 μm, diameter 13 mm) were obtained from Nalge Nunc International (Rochester, N.Y., USA). The reverse-phase HPLC using a Vydac protein and peptide column (218TP510; 5 μm, 250×10 mm) was performed as previously described[21].

MicroPET scans were performed on a microPET R4 rodent model scanner (Siemens Medical Solutions USA, Inc., Knoxville, Tenn., USA). The scanner has a computer-controlled bed and 10.8-cm transaxial and 8-cm axial fields of view (FOVs). It has no septa and operates exclusively in the three-dimensional (3-D) list mode. Animals were placed near the center of the FOV of the scanner.

Peptide Synthesis, Conjugation and Radiolabeling

NOTA-conjugated AE105 (NOTA-Asp-Cha-Phe-(D)Ser-(D)Arg-Tyr-Leu-Trp-Ser-COOH) was purchased from ABX GmbH. The purity was characterized using HPLC analysis and the mass was confirmed using matrix-assisted laser desorption/ionization time-of-flight mass spectrometry (MALDI-TOF-MS) (Se Suppl. FIG. 1A). The radiolabeling of NOTAAE105 with $^{18}$F—AlF is shown in FIG. 1 and was done according to a recently published protocol with minor modifications[26].

In brief, a QMA Sep-Pak Light cartridge (Waters, Milford, Ma, USA) was fixed with approximately 3 GBq of 18F-fluoride and then washed with 2.5 ml of metal free water. Na18F was then eluted from the cartridge with 1 ml saline, from which 100 μl fraction was taken. Then amounts of 50 μl 0.1 M Na-Acetate buffer (pH=4), 3 μl 0.1 M AlCl$_3$ and 100 μl of Na$^{18}$F in 0.9% saline (300 MBq) were first reacted in a 1 ml centrifuge tube (sealed) at 100° C. for 15 min. The reaction mixture was cooled. 50 μl ethanol and 30 nmol NOTA-AE105 in 3 μl DMSO were added and the reaction mixture were heated to 95° C. for 5 min. The crude mixture was purified with a semi-preparative HPLC. The fractions containing $^{18}$F—AlF-NOTA-AE105 were collected and combined in a sterile vial. The product was diluted in phosphate-buffered saline (PBS, pH=7.4) so any organic solvents were below 5% (v/v) and used for in vivo studies.

Cell Line and Animal Model

Human prostate cancer cell line PC-3 was obtained from the American Type Culture Collection (Manassas, Va., USA) and culture media DMEM was obtained from Invitrogen Co. (Carlsbad, Calif., USA). The cell line was cultured in DMEM supplemented with 10% (v/v) fetal bovine serum and 1% (v/v) penicillin/Streptomycin at 37° C. and 5% CO$_2$. Xenografts of human PC-3 prostate cancer cells were established by injection of 200 μl cells (1×10$^8$ cells/ml) suspended in 100 μl Matrigel (BO Biosciences, San Jose, Calif., USA), subcutaneously in the right flank of male nude mice obtained from Charles River Laboratory (Wilmington, Mass. USA), Tumors were allowed to grow to a size of 200-500 mg (3-4 weeks).

MicroPET Imaging

Three min static PET scans were acquired 0.5, 1.0 and 2.0 h post injection (p.i) of [18]F AlF-NOTA-AE105 via tail-vein injection of 2-3 MBq (n=4). Similar, the blocking study was performed by injection of the ligand together with 100 μg of AE152 (uPAR antagonist) through the tail vein (n=4) and PET scanned at the same time points. During each three minutes PET scan, mice were anesthetized with isoflurane (5% induction and 2% 30 maintenance in 100% $O_2$). Images were reconstructed using a two-dimensional ordered subsets expectation maximization (OSEM-2D) algorithm. No background correction was performed. All results were analyzed using Inveon software (Siemens Medical Solutions) and PET data was expressed as percent of injected dose per gram tissue (% ID/g) based on manual region-of-interest drawing on PET images and the use of a calibration constant. An assumption of a tissue density of 1 g/ml was used. No attenuation correction was performed.

Biodistribution Studies

After the last PET scan, all PC-3 bearing mice were euthanized. Blood, tumor and major organs were collected (wet-weight) and the radioactivity was measured using a y-counter from Perkin Elmer, MA, USA (N=4 mice/group).

uPAR ELISA uPAR ELISA on resected PC-3 tumors was done as described previously in detail[15]. All results were performed as duplicate measurements.

Statistical Analysis

All quantitative data are expressed as mean±SEM (standard error of the mean) and means were compared using Student t-test. Correlation statistics was done using linear regression analysis. A P-value of s 0.05 were considered statistically significant.

uPAR Binding Affinity

The uPAR binding affinity of AE105 and AE152[27] (used for blocking studies) was in this 20 study found to be 14.1 nM and 2.9 nM, respectively (FIG. 1A). A high uPAR binding affinity for AE105 with different chelators conjugated in the N-terminal, including the NOTA analogue NODAGA, has been confirmed in our previously studies[15,16], thus confirming the ability to make modifications in the N-terminal of AE105 without losing affinity towards human uPAR[14,27,28].

Radiochemistry

The $^{18}$F-labeling of NOTA-AE105 was synthesized based on a recently published procedure with some modification (FIG. 1B). During our labeling optimization, we found that 33% ethanol (v/v) was optimal using 30 nmol NOTA-AE105. We first formed the 18F—AlF complex in buffer at 100° C. for 15 min. Secondly was the NOTA-conjugated peptide added and incubated together with Ethanol at 95° C. for 5 min. By adding ethanol we were able to increase the overall yield to above 92.7% (FIG. 2C), whereas the yield without ethanol was only 30.4%, with otherwise same conditions. No further increase in the overall yield was observed using longer incubation time and/or different ethanol concentrations or using less than 30 nmol conjugated peptide. Two isomers were observed for [18]F—AlF-NOTA-AE105.

Figure 2:
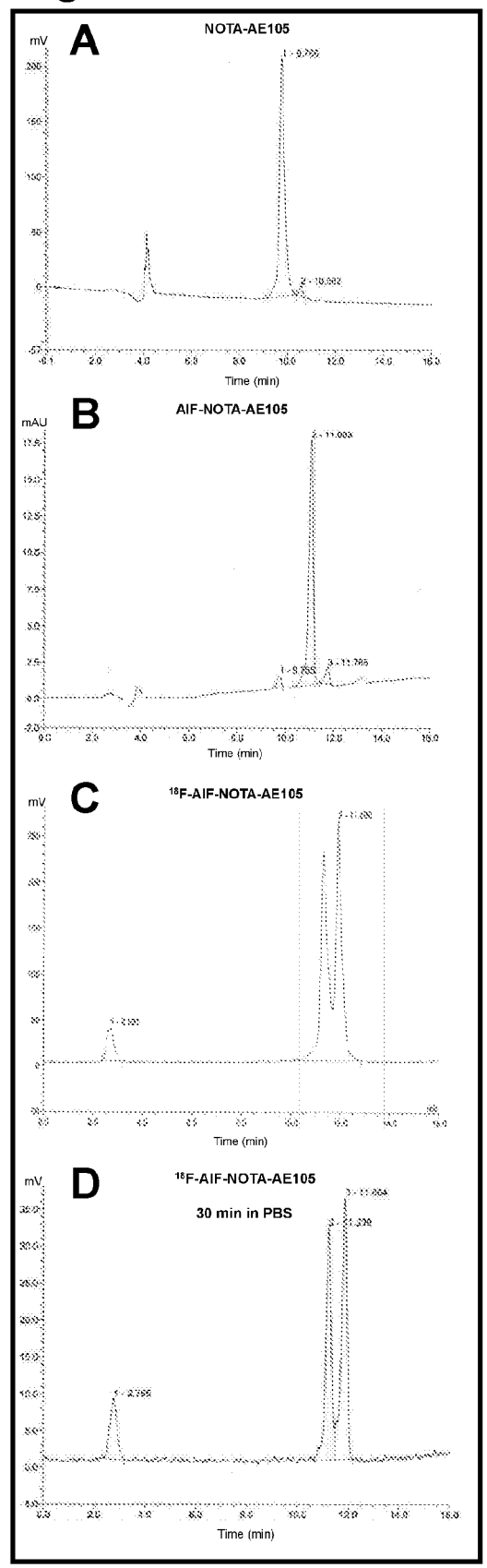
FIG. 2 shows representative HPLC UV chromatograms of NOTA-AE105 (A), cold standard AlF-NOTA-AE105 (B) and radio chromatograms for the final product $^{18}$F—AlF-NOTA-AE105 (C) and after 30 min in PBS (D).

In order to ensure the formation of the right product, a cold standard of the final product was synthesis (AlF-NOTA-AE105). The HPLC analysis of the precursor (NOTA-AE105, FIG. 2A) confirmed the purity of the NOTA-conjugated precursor (>97%) and MALDI-MS confirmed the mass (1511.7 Da) (See suppl. FIG. 1). The cold standard (AlFNOTA-AE105, FIG. 2B), with the right mass confirmed by MALDI-MS (1573.6 Da) (See suppl. FIG. 1B), corresponded well in regards to retention time with the 'hot' product (FIG. 2C), thus confirming the formation of 18F—AlF-NOTA-AE105 (FIG. 2C). No degradation of the final product was found after 30 min in PBS (FIG. 2D). The radioactive peaks were collected and diluted in PBS and used for in vivo studies. The specific activity in the final product was above 25 GBq/μmol.

In Vivo PET Imaging

Figure 3:
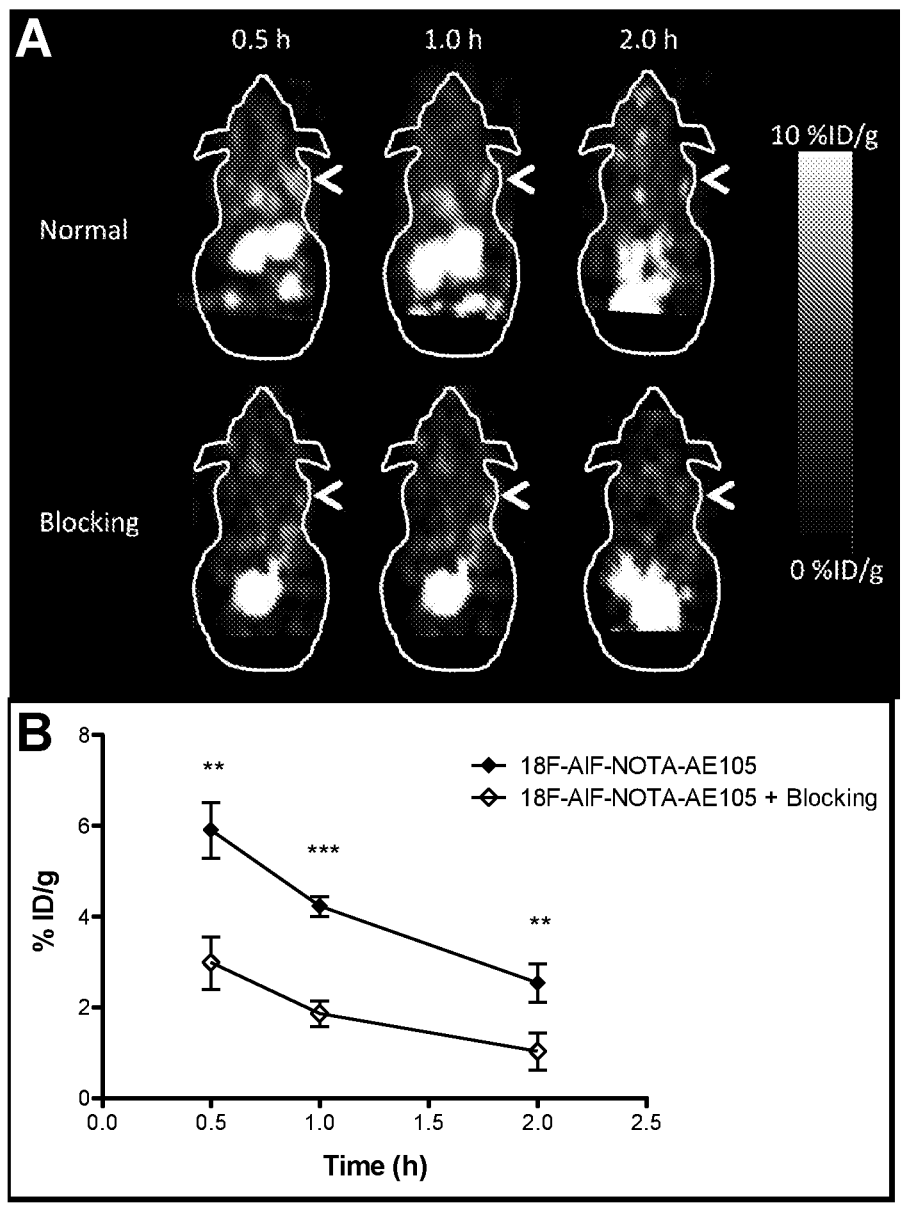
FIG. 3 shows: A. Representative PET images after 0.5 h, 1.0 h and 2.0 h p.i of $^{18}$F—AlF-NOTA-AE105 (top) and $^{18}$F—AlF-NOTA-AE105 with a blocking dose of AE152. White arrows indicate tumor. B. Quantitative ROI analysis with tumor uptake values (% ID/g). A significant higher tumor uptake was found at all three time points. Results are shown as % ID/g±SEM (n=4 mice/group).  $p<0.01$, * $p<0.001$ vs blocking group at same time point.

[18]F—AlF-NOTA-AE105 was injected i.v. in four mice bearing PC-3 tumors and PET scan were performed 0.5, 1.0 and 2.0 h post injection (p.i). Tumor lesions were easily identified from the reconstructed PET images (FIG. 3A) and ROI analysis revealed a high tumor uptake, with 5.90±0.35% ID/g after 0.5 h, declining to 4.22±0.13% ID/g and 2.54±0.24% ID/g after 1.0 and 2.0 h, respectively (FIG. 3B).

In order to ensure that the found tumor uptake did indeed reflect specific uPAR mediated uptake, four new PC-3 tumor bearing mice were then injected with a mixed solution containing [18]F—AlF-NOTA-AE105 and 100 μg of the high-affinity uPAR binding peptide denoted AE152, in order to see if the tumor uptake could be inhibited. A significant lower amount of [18]F—AlF-NOTA-AE105 tumor uptake was found at all three time points investigate (FIG. 3B) and tumor lesions were not as easily identified in the PET images (FIG. 3A). At 1.0 h p.i a tumor uptake of 1.86±0.14% ID/g was found in the blocking group compared with 4.22±0.13% ID/g found in the group of mice receiving only [18]F—AlFNOTA-AE105 (p<0.001, 2.3 fold reduction).

Biodistribution

Figure 4:
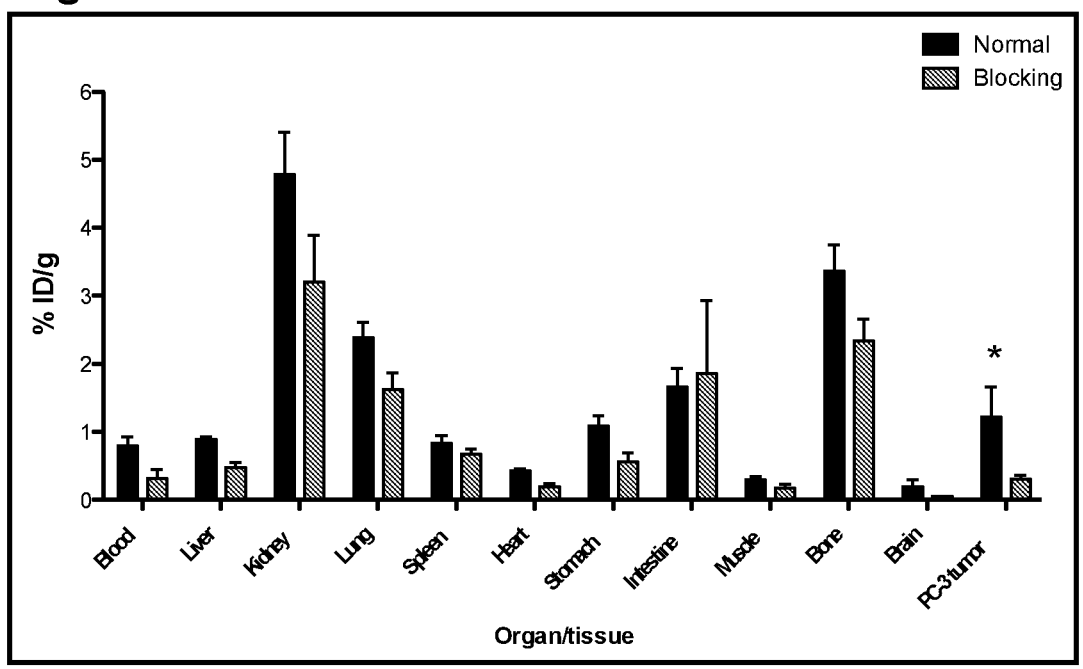
FIG. 4 shows biodistribution results for $^{18}$F—AlF-NOTA-AE105 (normal) and $^{18}$F-+blocking dose of AE152 (Blocking) in nude mice bearing PC-3 tumors at 2.5 h p.i. Results are shown as % ID/g±SEM (n=4 mice/group). * $p<0.05$ vs blocking group.

After the last PET scan, each group of mice where euthanized and selected organs and tissues were collected to investigate the biodistribution profile 2.5 h p.i. (FIG. 4). A significant higher tumor uptake in the group of mice receiving [18]F—AlF-NOTA-AE105 was found compared with blocking group (1.02±0.37% ID/g vs. 0.30±0.06% ID/g, p<0.05), thus confirming the specificity of [18]F—AlF-NOTA-AE105 for human uPAR found in the PET study. Highest activity was found in the kidneys for both groups of mice, confirming the kidneys to be the primarily route of excretion. Beside kidneys, the bone, well known to accumulate fluoride, also had a relatively high uptake of 3.54±0.32% ID/g and 2.34±0.33% ID/g for normal and blocking group, respectively.

uPAR Expression

Figure 5:
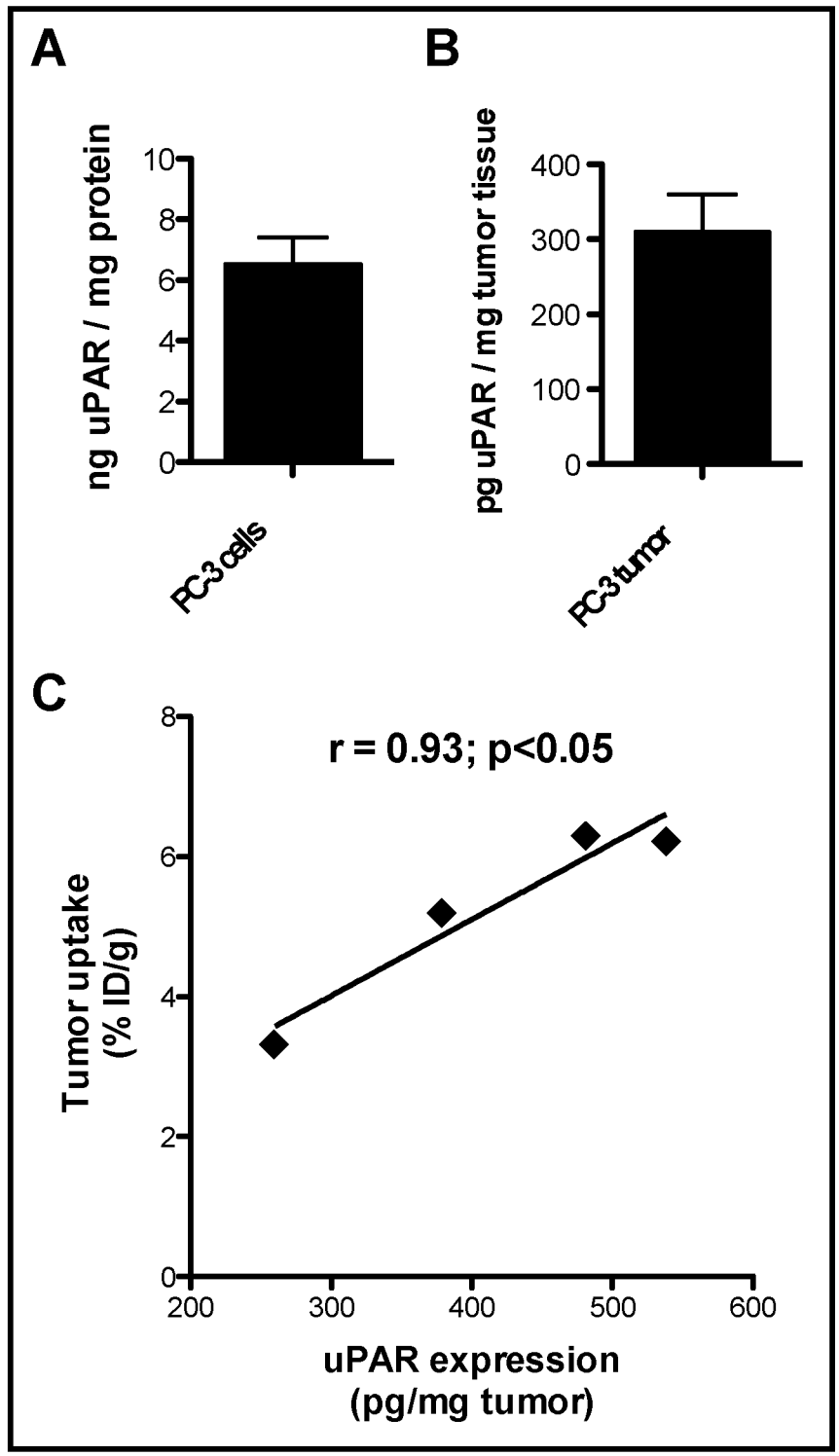
FIG. 5 shows uPAR expression level found using ELISA in PC-3 cells (A) and in resected PC-3 tumors (B). (C) A significant correlation between uPAR expression and tumor uptake was found in the four mice injected with 18F—AlF-NOTA-AE105 ($p<0.05$, r=0.93, n=4 tumors).

Both the PC-3 cells used for tumor inoculation and all PC-3 tumors at the end of the study (n=8) were finally analyzed for confirming expression of human uPAR (FIG. 5). An expression in the cells of 6.53±1.6 ng/mg protein was found (FIG. 5A), whereas the expression level in the resected tumors was 302±129 pg/mg tumor tissue (FIG. 5B). A significant correlation between tumor uptake of 18F—AlF-NOTA-AE105 and uPAR expression was found (p<0.05, r=0.93) (FIG. 5C).

Data Interpretation

The above experiments provide evidence for the applicability of an 18F-labeled ligand for 15 uPAR PET. The ligand was characterized in a human prostate cancer xenograft mouse model. Based on the obtained results, similar tumor uptake, specificity and tumor-to-background contrast were found compared to our previously published studies using 64Cu- and 68Ga-based ligands for PET[15,16]. Based on the superior physical characteristics of 18F and the high tumor-to-background contrast found already after 1 h p.i, our new 18F-based ligand must be considered the so far most promising uPAR PET candidate for translation into clinical use in order to non-invasively characterize invasive potential of e.g. prostate cancer.

$^{18}$F-labeling of peptides using the AlF-approach has previously been described to be performed at 100° C. for 15 min, at pH=4[17-20]. This protocol was modified, since degradation of the NOTA-conjugated peptide was observed using these conditions. The present inventors therefore first produced the $^{18}$F—AlF complex using the above mentioned conditions and next added the NOTA-conjugated peptide and lowered the temperature to 95° C., and within 5 min obtained a labeling yield of 92.7% and with no degradation of the peptide. Two isomers of $^{18}$F—AlF-NOTA-AE105 were produced. Same observations have been reported by others for $^{18}$F—AlF-NOTA-Octreotide[18] and all NOTA-conjugated IMP peptide analogues described[19]. The ratio of the two peaks were nearly constant for each labeling and both radioactive peaks were collected and used for further in vivo studies. This approach was recently also described by others[26].

Besides optimizing the temperature and time, the present inventors found that the addition of ethanol, to a final concentration of 33% (v/v), resulted in a significant higher labeling yield, compared with radiolabeling without ethanol (30.4% vs 92.7%), using the same amount of NOTA-conjugated peptide. Same observations have recently been described by others[26]. Here the effect of lowering the ionic strength was investigated using both acetonitrile, ethanol, dimethylforamide (DMF) and tetrahydrofuran (THF) at different concentrations. A labeling yield of 97% was reported using ethanol at a concentration of 80% (v/v). However, they used between 76-383 nmol NOTA-conjugated peptide, whereas in this study only used 30 nmol was used. The amount needed for optimal labeling yield therefore seems to be dependent on the peptide and on the amount of peptide used for labeling.

The tumor uptake of $^{18}$F—AlF-NOTA-AE105 was similarly compared with previously published results pertaining to $^{64}$Cu-based ligands[15]. The tumor uptake 1 h p.i was 4.79±0.7% ID/g, 3.48±0.8% ID/g and 4.75±0.9% ID/g for $^{64}$Cu-DOTA-AE105, $^{64}$Cu-CB-TE2A-AE105, $^{64}$Cu-CB-TE2A-PA-AE105 compared to 4.22±0.1% ID/g for $^{18}$F—AlF-NOTA-AE105. However, all $^{64}$Cu-based ligands were investigated using the human glioblastoma cell line U87MG, whereas in this study, the prostate cancer cell line PC-3 was used. Considering that the data show that the level of uPAR in the two tumor types is not similar, with PC-3 having around 300 μg uPAR/mg tumor tissue (FIG. 5B) and U87MG having approximately 1,700 μg/mg tumor tissue (unpublished), the tumor uptake of $^{18}$F—AlF-NOTA-AE105 seems to be relatively higher per pg uPAR, However, a direct comparison between the two independent studies is difficult, considering the different cancer cell line used. However, the present inventors have previously shown a significant correlation between uPAR expression and tumor uptake across three tumor types[15], which is confirmed in the present study using PC-3 xenografts (FIG. 5C), further validating the ability of $^{18}$F—AlF-NOTA-AE105 to quantify uPAR expression using PET imaging. The uPAR specific binding of $^{18}$F—AlF-NOTA-AE105 in the present study was confirmed by a 2.3-fold reduction in tumor uptake of $^{18}$F—AlF-NOTA-AE105 1 h p.i. when co-administration of an uPAR antagonist (AE152) was performed for blocking study.

The biodistribution study of 18F—AlF-NOTA-AE105 confirmed the kidneys to be the primary route of excretion and the organ with highest level of activity (FIG. 4). Same excretion profiles have been found for $^{68}$Ga-DOTA/NODAGA-AE105[16], $^{177}$Lu-DOTAAE105[30]. Besides the kidneys and tumor, the bone also had a relatively high accumulation of activity. Bone uptake following injection of 18F-based ligands is a well-described phenomenon and used clinically in NaF bone scans[31]. A bone uptake of 3.54% ID/g 2.5 h p.i was found, which is similar to the bone uptake following $^{18}$F-FDG injection in mice, where 2.49% ID/g have been reported 1.5 h p.i.[17].

The development of the first $^{18}$F-based ligand for uPAR PET provides of number of advantages compared to previously published $^{64}$Cu-based uPAR PET ligands. Considering the optimal tumor-to-background contrast as early as 1 h p.i. as found in this study and in previously studies using 64Cu, the relatively shorter half-life of $^{18}$F ($T_{1/2}$=1.83 h) compared with $^{64}$Cu ($T_{1/2}$=12.7 h) seems to be optimal consider the much lower radiation burden to future patients using $^{18}$F—AlF-NOTA-AE105. Moreover, is the production of $^{18}$F well established in a number of institutions worldwide, whereas the production of $^{64}$Cu still is limited to relatively few places.

Example 2

[$^{64}$Cu]NOTA-AE105 (NOTA-Asp-Cha-Phe-Ser-Arg-Tyr-Leu-Trp-Ser-OH)

$^{64}$CuCl2 dissolved in 50 ul metal-free water was added to a solution containing 10 nmol NOTA-AE105 and 2.5 mg gentisic acid dissolved in 500 ul 0.1 M NH4OAc buffer (pH 5.5) and left at room temperature for 10 minutes resulting in 375 MBq [64Cu]NOTA-AE105 20 with a radiochemical purity above 99%. The radiochemical purity decreased to 94% after 48 hours storage.

Example 3

Figure 6:
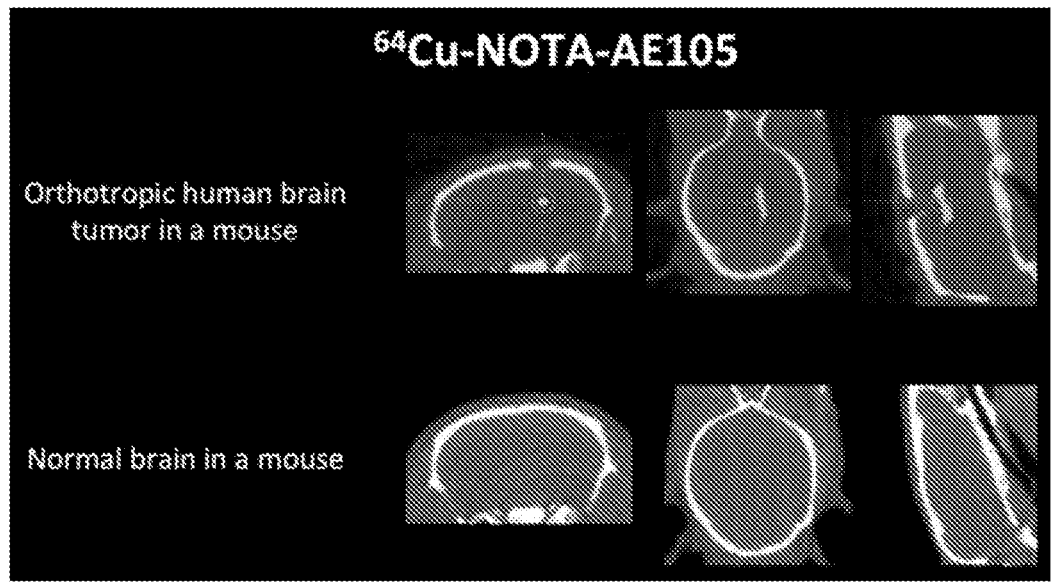
FIG. 6 shows in vivo uPAR PET imaging with [$^{64}$Cu] NOTA-A.E105 in a orthotropic human glioblastoma mouse model
Figure 6:
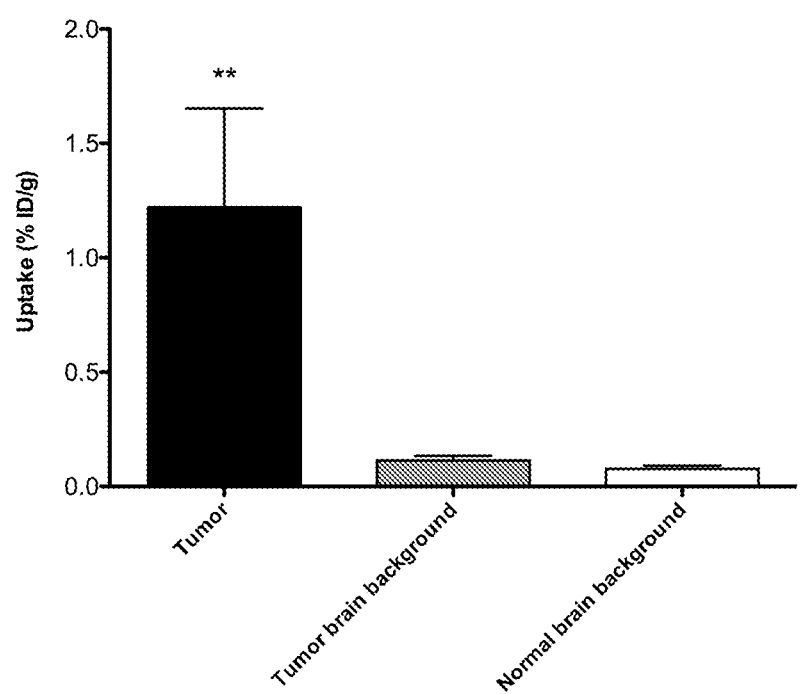

In Vivo uPAR PET Imaging with [$^{64}$Cu]NOTA-AE105 in a Orthotropic Human Glioblastoma Mouse Model A mouse was inoculated with human derived glioblastoma cells in the brain. 3 weeks later a small tumor was visible using microCT scan A microPET images was recorded 1 hr post i.v. injection of approximately 5 MBq [$^{64}$Cu]NOTA-AE105. Uptake in the tumor and background brain tissue was quantified. Moreover, was a control mouse (with no tumor inoculated) also PET scanned using the same procedure, to investigate the uptake in normal brain tissue with intact blood brain barrier. See FIG. 6.

Example 4

[68Ga]NOTA-AE105 (NOTA-Asp-Cha-Phe-Ser-Arg-Tyr-Leu-Trp-Ser-OH)

A 1 ml fraction of the eluate form a $^{68}$Ge/68Ga generator for added to a solution containing 20 nmol NOTA-AE105 dissolved in 1000 ul 0.7M NaOAc buffer (pH 3.75) and heated to 60° C. for 10 minutes. The corresponding mixture could be purified on a C18 SepPak column resulting in 534 MBq [$^{68}$Ga]NOTA-AE105 with a radiochemical purity above 98%.

Example 5

In Vivo uPAR PET Imaging with [$^{68}$Ga]NOTA-AE105 in a Orthotropic Human Glioblastoma Mouse Model A mouse was inoculated with human derived glioblastoma cells in the brain. 3 weeks 15 later a small tumor was visible using microCT scan A microPET images was recorded 1 hr post i.v. injection of approximately 5 MBq

Figure 7:
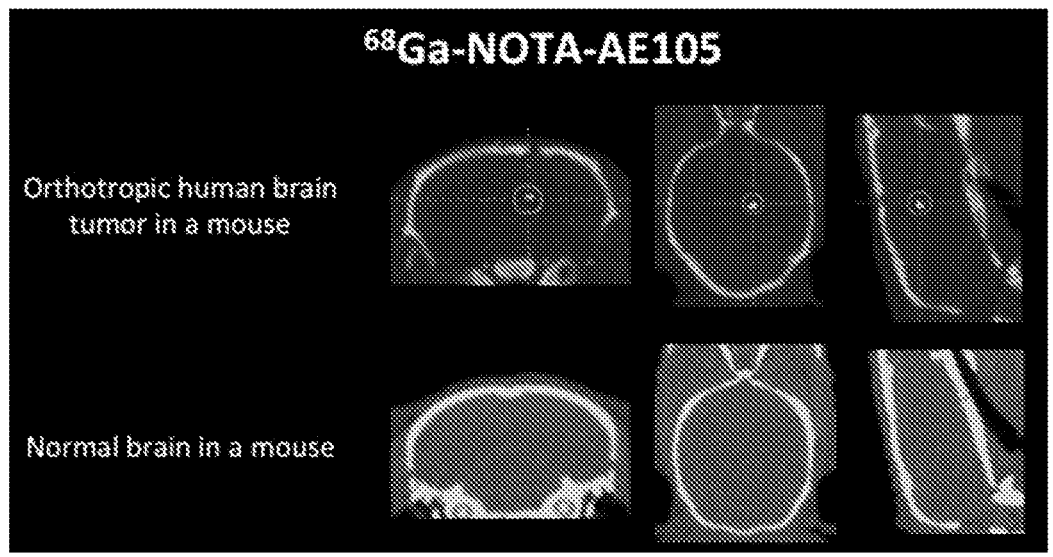
FIG. 7 shows in vivo uPAR PET imaging with [$^{68}$Ga] NOTA-AE105 in a orthotropic 5 human glioblastoma mouse model.
Figure 7:
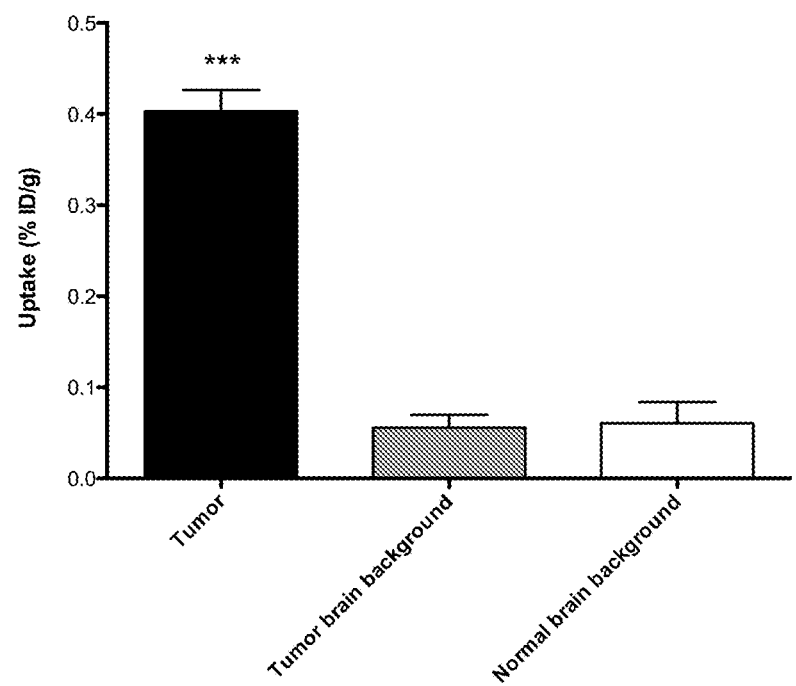
Figure 8:
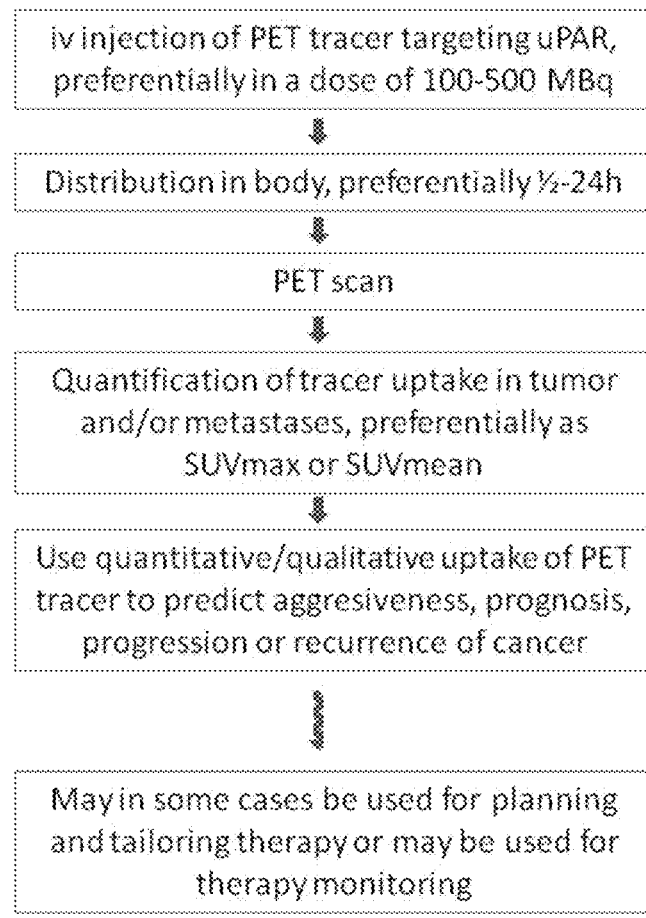
FIG. 8 shows a flow diagram summarizing the steps carried out in accordance with the present invention.

[68Ga]NOTA-AE105. Uptake in the tumor and background brain tissue was quantified. Moreover, was a control mouse (with no tumor inoculated) also PET scanned using the same procedure, to investigate the uptake in normal brain tissue with intact blood brain barrier. See FIG. 7.

REFERENCES

1. Rasch M G, Lund I K, Almasi C E, Hoyer-Hansen G. Intact and cleaved uPAR forms: diagnostic and prognostic value in cancer. *Front Biosci*. 2008; 13:6752-6762.
2. Miyake H, Hara I, Yamanaka K, Arakawa S, Kamidono S. Elevation of urokinasetype-plasminogen activator and its receptor densities as new predictors of disease progression and prognosis in men with prostate cancer. *Int J Oncol*. March 1999; 14(3):535-541.
3. Miyake H, Hara I, Yamanaka K, Gohji K, Arakawa S, Kamidono S. Elevation of serum levels of urokinase-type plasminogen activator and its receptor is associated with disease progression and prognosis in patients with prostate cancer. *Prostate*. May 1999; 39(2): 123-129.
4. Piironen T, Haese A, Huland H, et al. Enhanced discrimination of benign from malignant prostatic disease by selective measurements of cleaved forms of urokinase receptor in serum. *Clin Chem*. May 2006; 52(5):838-844.
5. Steuber T, Vickers A, Haese A, et al. Free PSA isoforms and intact and cleaved forms of urokinase plasminogen activator receptor in serum improve selection of patients for prostate cancer biopsy. *Int J Cancer*. Apr. 1, 2007; 120(7):1499-1504.
6. Gupta A, Lotan Y, Ashfaq R, et al. Predictive value of the differential expression of the urokinase plasminogen activation axis in radical prostatectomy patients. *Eur Urol*. May 2009; 55(5):1124-1133.
7. Kjellman A, Akre O, Gustafsson O, et al. Soluble urokinase plasminogen activator receptor as a prognostic marker in men participating in prostate cancer screening. *J Intern Med*. March 2011; 269(3):299-305.
8. Nogueira L, Corradi R, Eastham J A. Other biomarkers for detecting prostate cancer. *BJU Int*. January 2010; 105(2): 166-169.
9. Shariat S F, Semjonow A, Lilja H, Savage C, Vickers A J, Bjartell A. Tumor markers in prostate cancer I: blood-based markers. *Acta Oncol*. June 2011; 50 Suppl 1:61-75.
10. Shariat S F, Roehrborn C G, McConnell J D, et al. Association of the circulating levels of the urokinase system of plasminogen activation with the presence of prostate cancer and invasion, progression, and metastasis. *J Clin Oncol*. Feb. 1, 2007; 25(4):349-355.
11. Rabbani S A, Ateeq B, Arakelian A, et al. An anti-urokinase plasminogen activator receptor antibody (ATN-658) blocks prostate cancer invasion, migration, growth, and experimental skeletal metastasis in vitro and in vivo. *Neoplasia*. October 2010; 12(10):778-788.
12. Pulukuri S M, Gondi C S, Lakka S S, et al. RNA interference-directed knockdown of urokinase plasminogen activator and urokinase plasminogen activator receptor inhibits prostate cancer cell invasion, survival, and tumorigenicity in vivo. *J Biol Chem*. Oct. 28, 2005; 280(43):36529-36540.
13. Margheri F, D'Alessio S, Serrati S, et al. Effects of blocking urokinase receptor signaling by antisense oligonucleotides in a mouse model of experimental prostate cancer bone metastases. *Gene Ther*. April 2005; 12(8): 702-714.
14. Kriegbaum M C, Persson M, Haldager L, et al. Rational targeting of the urokinase receptor (uPAR): development of antagonists and non-invasive imaging probes. *Curr Drug Targets*. November 2011; 12(12): 1711-1728.
15. Persson M, Madsen J, Ostergaard S, et al. Quantitative PET of human urokinase-type plasminogen activator receptor with 64Cu-DOTA-AE105: implications for visualizing cancer invasion. *J Nucl Med*. January 2012; 53(1): 138-145.
16. Persson M, Madsen J, Ostergaard S, Ploug M, Kjaer A. (68)Ga-labeling and in vivo evaluation of a uPAR binding DOTA- and NODAGA-conjugated peptide for PET imaging of invasive cancers. *Nucl Med Biol*. May 2012; 39(4):560-569.
17. McBride W J, Sharkey R M, Karacay H, et al. A novel method of 18F radiolabeling 20 for PET. *J Nucl Med*. June 2009; 50(6):991-998.
18. Laverman P, McBride W J, Sharkey R M, et al. A novel facile method of labeling octreotide with (18)F-fluorine. *J Nucl Med*. March 2010; 51 (3):454-461.
19. McBride W J, D'Souza C A, Sharkey R M, et al. Improved 18F labeling of peptides with a fluoride-aluminum-chelate complex. *Bioconjug Chem*. Jul. 21, 2010; 21(7):1331-1340.
20. D'Souza C A, McBride W J, Sharkey R M, Todaro L J, Goldenberg O M. High-yielding aqueous 18F-labeling of peptides via Al18F chelation. *Bioconjug Chem*. Sep. 21, 2011; 22(9):1793-1803.
21. Liu S, Liu H, Jiang H, Xu Y, Zhang H, Cheng Z. One-step radiosynthesis of (1)(8)F—AlF-NOTA-RGD(2) for tumor angiogenesis PET imaging. *Eur J Nucl Med Mol Imaging*. September 2011; 38(9):1732-1741.
22. Gao H, Lang L, Guo N, et al. PET imaging of angiogenesis after myocardial infarction/reperfusion using a one-step labeled integrin-targeted tracer 18F—AlF-NOTAPRGD2. *Eur J Nucl Med Mol Imaging*. April 2012; 39(4):683-692.
23. Dijkgraaf I, Franssen G M, McBride W J, et al. PET of tumors expressing gastrin-releasing peptide receptor with an 18F-labeled bombesin analog. *J Nucl Med*. June 2012; 53(6):947-952.
24. Heskamp S, Laverman P, Rosik D, et al. Imaging of human epidermal growth factor receptor type 2 expression with 18F-labeled affibody molecule ZHER2:2395 in a mouse model for ovarian cancer. *J Nucl Med*. January 2012; 53(1):146-153.
25. Hoigebazar L, Jeong J M, Lee J Y, et al. Syntheses of 2-nitroimidazole derivatives conjugated with 1,4,7-triazacyclononane-N,N'-di acetic acid labeled with F-18 using an aluminum complex method for hypoxia imaging. *J Med Chem*. Apr. 12, 2012; 55(7):3155-3162.
26. Laverman P, D'Souza C A, Eek A, et al. Optimized labeling of NOTA-conjugated octreotide with F-18. *Tumour Biol*. April 2012; 33(2):427-434.
27. Ploug M, Ostergaard S, Gardsvoll H, et al. Peptide-derived antagonists of the urokinase receptor. affinity maturation by combinatorial chemistry, identification of functional epitopes, and inhibitory effect on cancer cell intravasation. *Biochemistry*. Oct. 9, 2001; 40(40):12157-12168.
28. Ploug M. Structure-function relationships in the interaction between the urokinase-type plasminogen activator and its receptor. *Curr Pharm Des*. 2003; 9(19): 1499-1528.
29. McBride W J, D'Souza C A, Sharkey R M, Goldenberg O M. The radiolabeling of proteins by the [18F]AlF method. *Appl Radiat Isot*. January 2012; 70(1):200-204.
30. Persson M, Rasmussen P, Madsen J, Ploug M, Kjaer A. New peptide receptor radionuclide therapy of invasive cancer cells: in vivo studies using (177)Lu-DOTA-AE105 targeting uPAR in human colorectal cancer xenografts. *Nucl Med Biol*. Jun. 25, 2012.

31. Kurdziel K A, Shih J H, Apolo A B, et al. The Kinetics and Reproducibility of 18F Sodium Fluoride for Oncology Using Current PET Camera Technology. *J Nucl Med*. August 2012; 53(8): 1175-1184.

The invention claimed is:

1. A method of generating images of uPAR expression in a human or animal body by diagnostic imaging of uPAR expressing tumors involving administrating an imaging agent to said body, and generating an image of at least a part of said body to which said imaging agent is administrated;
wherein the imaging agent is a positron-emitting radionuclide labelled peptide conjugate, said conjugate comprising a uPAR binding peptide coupled via the chelating agent NOTA to a $^{68}$Ga radionuclide;
wherein the uPAR binding peptide is selected from the group consisting of:
(D-Asp)-([beta]-cyclohexyl-L-alanine)-(Phe)-(D-Ser)-(D-Arg)-(Tyr)-(Leu)-(Trp)-(Ser),
(Ser)-(Leu)-([beta]-cyclohexyl-L-alanine)-(Phe)-(D-Ser)-(Gln)-(Tyr)(Leu)-(Trp)-(Ser),
(D-Glu)-([beta]-cyclohexyl-L-alanine)-(Phe)-(D-Ser)-(D-Tyr)-(Tyr)-(Leu)-(Trp)-(Ser),
(Asp)-([beta]-cyclohexyl-L-alanine)-(Phe)-(D-Ser)-(D-Arg)-(Tyr)-(Leu)-(Trp)-(Ser),
(Asp)-([beta]-cyclohexyl-L-alanine)-(Phe)-(Ser)-(D-Arg)-(Tyr)-Leu)-(Trp)-(Ser),
(D-Asp)-([beta]-cyclohexyl-L-alanine)-(Phe)-(Ser)-(D-Arg)-(Tyr)-Leu)-(Trp)-(Ser),
(D-Thr)-([beta]-cyclohexyl-L-alanine)-(Phe)-(D-Ser)-(D-Arg)-(Tyr)-(Leu)-(Trp)-(Ser),
(D-Asp)-([beta]-cyclohexyl-L-alanine)-(Phe)-(D-Ser)-(D-Arg)-(Tyr)-(Leu)-([beta]-2-naphthyl-L-alanine)-(Ser),
(Asp)-([beta]-cyclohexyl-L-alanine)-(Phe)-(D-Ser)-(Arg)-(Tyr)-(Leu)-(Trp)-(Ser),
(Asp)-([beta]-cyclohexyl-L-alanine)-(Phe)-(D-Ser)-(D-Arg)-(Tyr)-(Leu)([beta]-1-naphthyl-L-alanine)-(Ser),
(D-Glu)-([beta]-cyclohexyl-L-alanine)-(Phe)-(D-Ser)-(Tyr)-(Tyr)-(Leu)-(Trp)-(Ser),
(Asp)-([beta]-cyclohexyl-L-alanine)-(Phe)-(D-Ser)-(D-Arg)-(Leu)-(Leu)-(Trp)-(D-His),
(Asp)-([beta]-cyclohexyl-L-alanine)-(Phe)-(D-Ser)-(D-Arg)-([beta]-cyclohexyl-L-alanine)-(Leu)-(Trp)-(Ile),
(Asp)-([beta]-cyclohexyl-L-alanine)-(Phe)-(D-Ser)-(D-Arg)-(Tyr)-(Leu)([beta]-1-naphthyl-L-alanine)-(D-His),
(Asp)-([beta]-cyclohexyl-L-alanine)-(Phe)-(D-Ser)-(D-Arg)-(N-(2,3-dimethoxybenzyl)glycine)-(D-Phe)-(N-(3-indolylethyl)glycine)-(N-(2-methoxyethyl)glycine),
(Asp)-([beta]-cyclohexyl-L-alanine)-(Phe)-(D-Ser)-(D-Arg)-(N-(2,3-dimethoxybenzyl)glycine)-(D-Phe)-(N-benzylglycine)-(N-(2[beta]thoxyethyl)glycine),
(Asp)-([beta]-cyclohexyl-L-alanine)-(Phe)-(D-Ser)-(D-Arg)-(N-(2,3-dimethoxybenzyl)glycine)-(D-Phe)-(N-(methylnaphthalyl)glycine)-(N-(2-methoxyethyl)glycine), and
(Asp)-([beta]-cyclohexyl-L-alanine)-(Phe)-(D-Ser)-(D-Arg)-(N-(2,3-dimethoxybenzyl)glycine)-(D-Phe)-(N-(2,3-dimethoxybenzyl)glycine)-(Ile) wherein the C-terminal is either a carboxylic acid or an amide;
wherein the conjugate is to be administered in a dose of 100-500 MBq followed by PET scanning ½-24 h after the conjugate has been administered, and quantification through SUVmax and/or SUVmean.

2. The method according to claim 1, wherein the peptide is (D-Asp)-([beta]-cyclohexyl-L-alanine)-(Phe)-(D-Ser)-(D-Arg)-(Tyr)-(Leu)-(Trp)-(Ser).

3. The method according to claim 1, wherein the imaging agent has the formula:

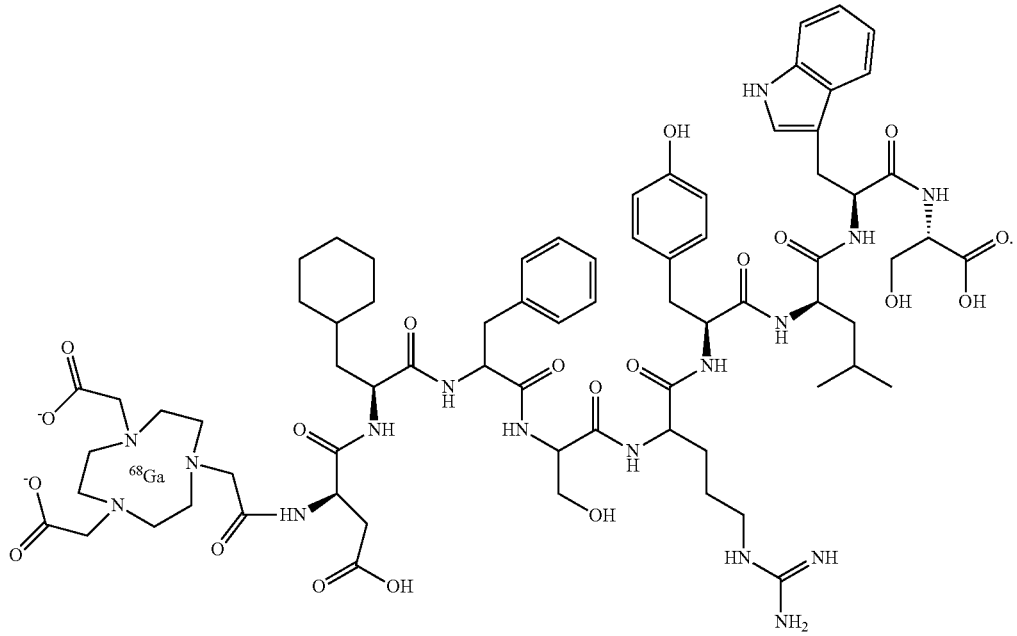

4. The method according to claim 1, wherein the cancer is selected from prostate, breast, pancreatic, lung, brain and colorectal cancer.

5. The method according to claim 1, wherein the imaging agent is provided in a pharmaceutical composition comprising the imaging agent, together with one or more pharmaceutical acceptable adjuvants, excipients or diluents.

6. The method according to claim 1, wherein the conjugate is administered in a dose of 200-400 MBq.

* * * * *